(12) United States Patent
Miller et al.

(10) Patent No.: US 8,187,294 B2
(45) Date of Patent: May 29, 2012

(54) ROTATING SURGICAL CUTTER

(75) Inventors: Michael E. Miller, Trafalgar, IN (US); Charles Butcher, Carmel, IN (US)

(73) Assignee: Suros Surgical Systems, Inc., Indianapolis, IN (US)

( * ) Notice: Subject to any disclaimer, the term of this patent is extended or adjusted under 35 U.S.C. 154(b) by 806 days.

(21) Appl. No.: 11/235,637

(22) Filed: Sep. 26, 2005

(65) Prior Publication Data
US 2007/0073326 A1     Mar. 29, 2007

(51) Int. Cl.
*A61B 17/22*     (2006.01)
(52) U.S. Cl. ......... 606/180; 606/171; 600/564; 600/567
(58) Field of Classification Search ........... 606/177, 606/178, 179, 180, 80, 81, 167–171; 600/562–568; 604/22, 57–64
See application file for complete search history.

(56) References Cited

U.S. PATENT DOCUMENTS

| | | | |
|---|---|---|---|
| 2,487,502 A * | 11/1949 | Willinsky | 606/46 |
| 2,850,007 A * | 9/1958 | Lingley | 600/567 |
| 3,995,619 A * | 12/1976 | Glatzer | 600/550 |
| 5,649,547 A | 7/1997 | Ritchart et al. | |
| 5,769,086 A * | 6/1998 | Ritchart et al. | 600/566 |
| 5,782,849 A * | 7/1998 | Miller | 606/159 |
| 5,928,164 A | 7/1999 | Burbank et al. | |
| 6,402,701 B1* | 6/2002 | Kaplan et al. | 600/567 |
| 6,468,228 B1* | 10/2002 | Topel et al. | 600/567 |
| 6,485,436 B1 | 11/2002 | Truckai et al. | |
| 6,749,576 B2 | 6/2004 | Bauer | |
| 2002/0103486 A1* | 8/2002 | Cucin | 606/49 |
| 2002/0193705 A1 | 12/2002 | Burbank et al. | |
| 2005/0065453 A1 | 3/2005 | Shabaz et al. | |

FOREIGN PATENT DOCUMENTS

WO    WO-2005/063126    7/2005

OTHER PUBLICATIONS

PCT International Search Report PCT/IB2006/053378 dated Mar. 28, 2007.

* cited by examiner

*Primary Examiner* — Tom Hughes
*Assistant Examiner* — David Eastwood
(74) *Attorney, Agent, or Firm* — Vista IP Law Group LLP

(57) ABSTRACT

A rotating surgical system is provided that includes a base, a first member rotably engaged with the base, and a second member fixed with said first member such that said first member and said second member rotate together.

11 Claims, 3 Drawing Sheets

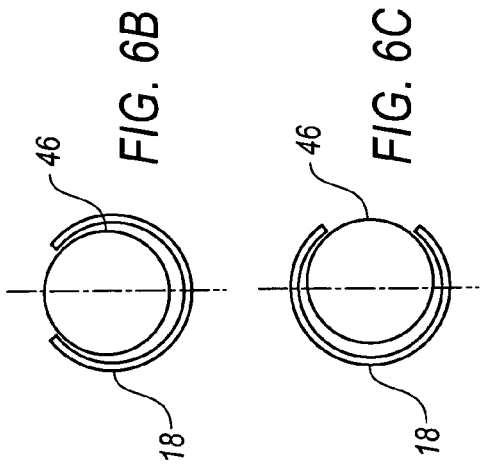
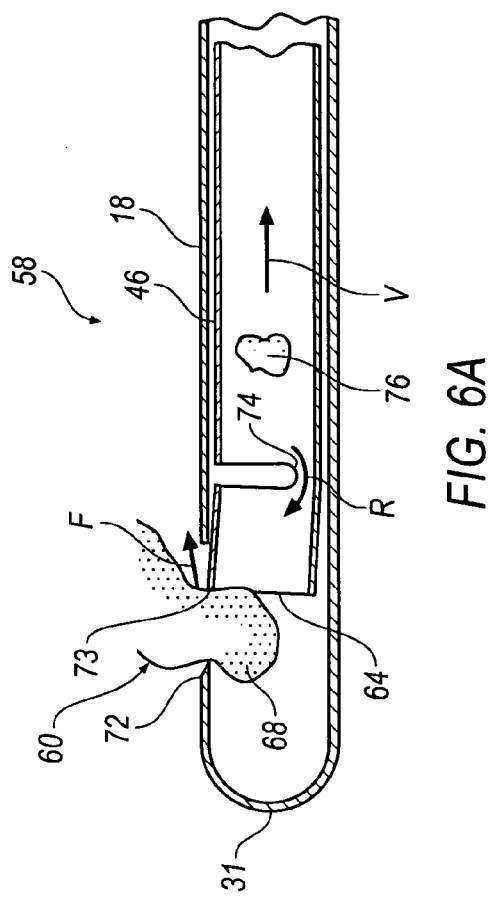
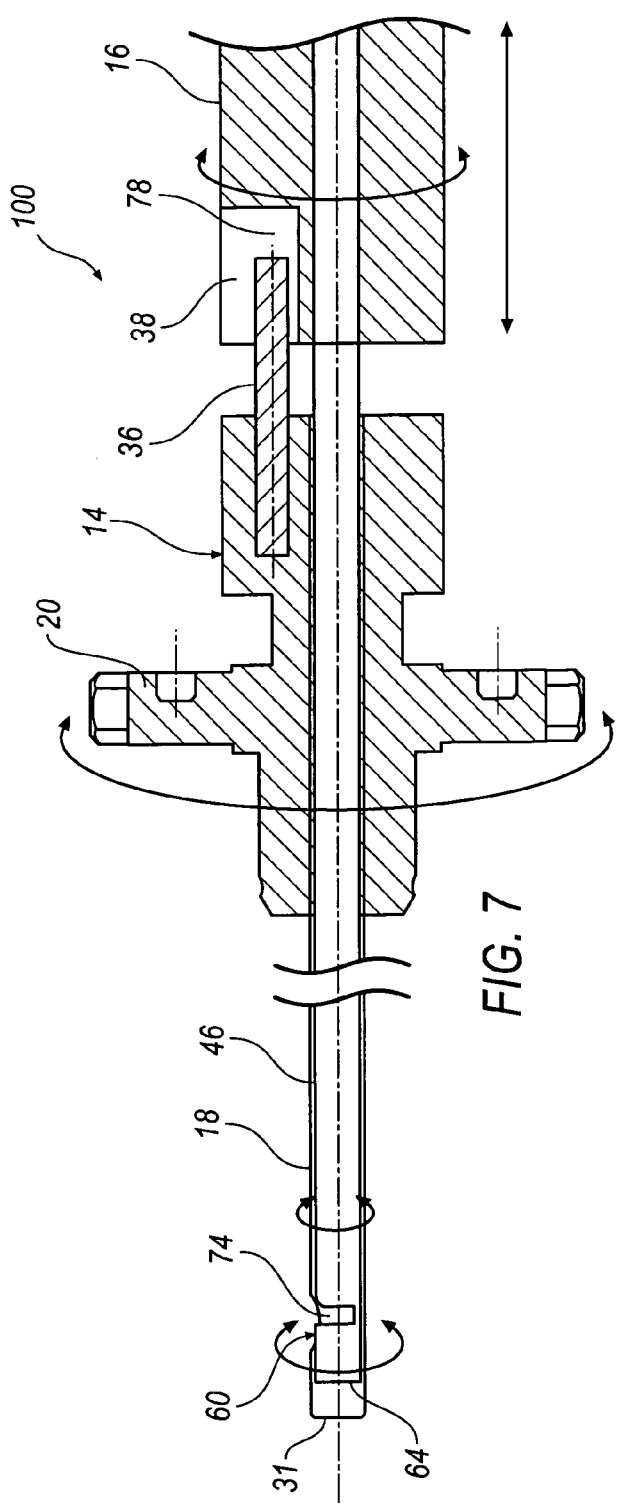

ROTATING SURGICAL CUTTER

FIELD OF THE INVENTION

The present invention relates generally to surgical devices and more particularly to maintaining alignment of co-axial cannulas in surgical devices.

BACKGROUND

Description of the Related Art

Surgical cutting systems, especially neurosurgery systems, are precise instruments for excising tissue from a patient. These systems generally require a surgeon to hand-position the instrument and guide the cutter to the appropriate location. Many handpieces for known surgical cutting systems are symmetrical in nature and do not lend themselves to prolonged use. However, where the handpiece has an ergonomic design with an asymmetric handle, the handpiece can be used with less discomfort and fatigue. But, when the cutter is a side opening type, to position a side opening cutter requires the surgeon to turn and hold the handpiece with an unintended and awkward grip on the handpiece. Typically, the tissue receiving opening is in a fixed orientation relative to the handle. Because the ergonomic handpiece was meant to be held in only definite orientations, holding the handpiece at an angle other than the intended orientation makes the handpiece awkward, less controllable, and non-ergonomic.

In addition to the handpiece design, known surgical cutting systems generally include a drive system for operating the cutter and a vacuum system for removing the excised tissue. The vacuum system may also assist the cutting operation by pulling tissue into the cutting opening/mouth near the blade. As the cutting mechanism severs tissue, the vacuum system then draws the tissue out, through a hose, to a collection canister.

When the instrument is a mechanical cutter, the cutting operation is generally achieved using a side opening mouth to receive the tissue. The cutting instrument may include a cannula within a cannula, or bi-cannular, device. The inner cannula reciprocates while the outer cannula has a side opening to receive tissue that is pulled in using a vacuum. However, for the cutting operation to be effective, the tissue receiving opening on the outer cannula must maintain orientation with the cutting member of the inner cannula. This is because the inner cannula may have a hinge near the cutting edge that is aligned with the tissue receiving opening. If the inner cannula cutting member is not aligned with the tissue receiving opening, excision of the tissue will not be effective. Because of misalignment issues, the surgeon may be required to make multiple attempts to sever the tissue.

Further, when the cutting instrument is used with an ergonomic handle, reorientation of the tissue receiving opening becomes awkward using a side opening cutter. To hold and position the instrument appropriately requires the handle to be selectively rotated in the surgeon's hand. This creates the undesirable situation where the ergonomic handle is used outside the intended orientations. The ergonomic design, that was intended to be comfortable to hold, then becomes more difficult to control than a standard symmetrical handpiece.

This leads to the problem that current ergonomic reciprocating cutters do not have the ability to rotate the inner and outer cannulae together to change the orientation of the tissue receiving opening. Thus, the handles are difficult to hold and manipulate when they are not used in their ergonomic positions. Additionally, when a cable powers the handpiece, rotation of the handpiece may be further impaired by the cable resisting the rotation.

Accordingly, an improved surgical device is required that facilitates rotation of the inner and outer cannulae together such that the tissue receiving opening and the inner cutting member maintain their relative position to each other. Further, an improved surgical device is required that allows for blade pivoting while maintaining the desired ergonomic holding position.

SUMMARY

A rotating surgical system is provided that includes a base, a first member engaged with the base, and a second member that is fixed with said first member such that said first member and said second member rotate together. The system may further provide that the second member reciprocates. The system may further include a drive shaft engaged with said second member, the drive shaft providing reciprocative motion to the second member.

In another embodiment, a rotating surgical system includes a base, a first member engaged with said base, a second member having a portion partially disposed within the first member, a guide that operatively connects the first member and the second member together, such that the guide rotates the second member in unison with the first member, and a drive member reciprocatingly engaging the second member.

In yet another embodiment, a rotating surgical instrument is disclosed that has a first member and a second member fixedly connected to the first member, such that the second member and the first member rotate synchronously. The instrument may further include a first cannula engaged with the first member and a second cannula engaged with the second member and partially disposed within the first member, such that the first cannula and the second cannula rotate together when said first member is rotated. The instrument may further include a tissue receiving opening formed in the first member, and a cutting portion disposed upon the second member that is aligned with the tissue receiving opening, wherein the instrument maintains alignment of said tissue receiving opening and said cutting portion relative to each throughout the range of rotation of the first and second cannulas.

In yet another embodiment, a rotating surgical instrument is provided that includes a first hub, a first member engaged with the first hub, a second hub, a second member engaged with the second hub, and a guide connecting the first hub and the second hub, whereby the first member and the second member maintain orientation with one another. The instrument may further provide at least part of the second member reciprocates within the first member.

BRIEF DESCRIPTION OF THE DRAWINGS

The features and inventive aspects of the present invention will become more apparent upon reading the following detailed description, claims, and drawings, of which the following is a brief description:

FIG. 6A is a cross-sectional view of a reciprocating cutter for use with the rotating surgical system of FIG. 1;

FIG. 6B is a cross-sectional view of a hinge and a tissue receiving opening in a first pivoting orientation taken along lines B-B of FIG. 6A;

FIG. 6C is a cross-sectional view of the hinge and tissue receiving opening in a second pivoting orientation; and FIG. 7 is a cross-sectional view of an embodiment of a tissue cutting system for use with the rotating surgical system of FIG. 1.

DETAILED DESCRIPTION

Figures 1, 2:
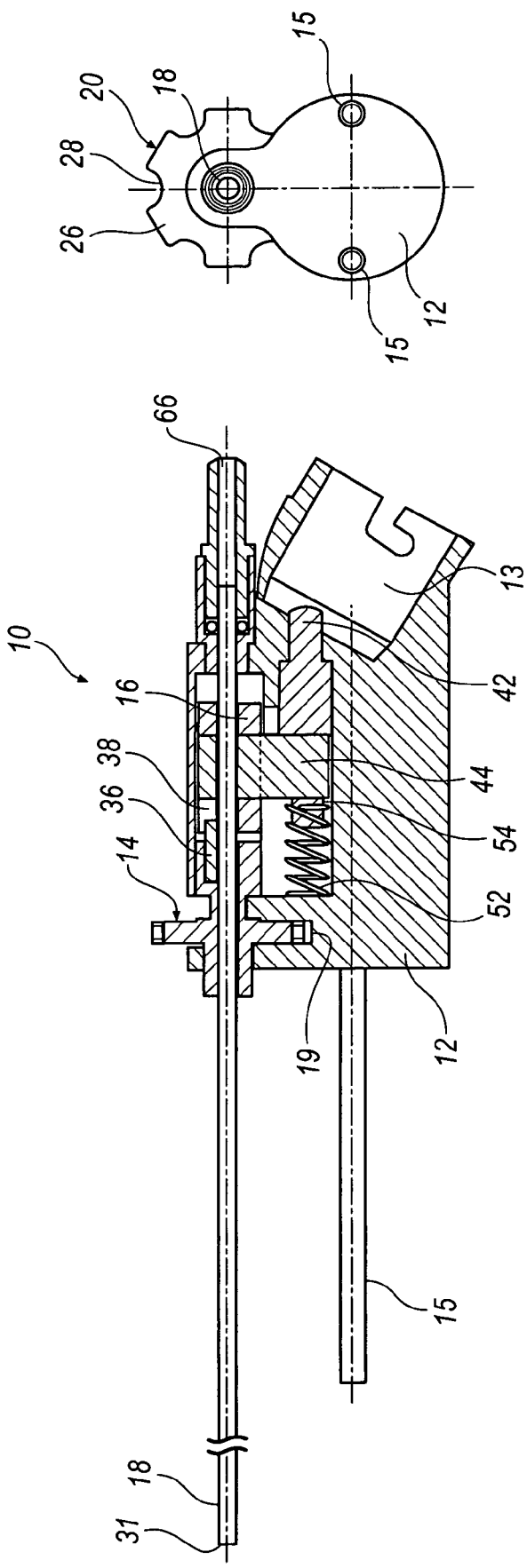
FIG. 1 is a simplified cross-sectional view of an embodiment of a rotating surgical system of the present invention.
FIG. 2 is a simplified front view of the rotating surgical system illustrated in FIG. 1.

Referring now to the drawings, preferred embodiments of the present invention are shown in detail. Although the drawings represent embodiments of the present invention, the drawings are not necessarily to scale and certain features may be exaggerated to better illustrate and explain the present invention. The embodiments set forth herein are not intended to be exhaustive or otherwise limit the invention to the precise forms disclosed in the following detailed description.

Referring to FIGS. 1-7, an embodiment of a rotating surgical system 10 in accordance with the present invention is shown. Rotating surgical system 10 includes a handpiece 12. Handpiece 12 acts as a base for engaging rotating surgical system 10 with a surgical environment. In one embodiment, handpiece 12 is a portion of an ergonomic system where a drive member (not shown) is locked into handpiece 12 at an angle to a drive receiver 13. The asymmetrical design of handpiece 12 allows for comfortable and accurate control of handpiece 12. While handpiece 12 is embodied as an ergonomic system allowing a surgeon to comfortably hold surgical system 10, handpiece 12 may further include one or more handpiece guides 15 to assist in the alignment of handpiece 12 with other medical equipment, such as an endoscope (not shown).

Connected to handpiece 12 is an outer hub 14, an inner hub 16, and an outer cannula 18. Outer hub 14 (best seen in FIG. 3), is mounted to handpiece 12 for selective rotational movement. More specifically, handpiece 12 includes a slot 19 into which a wheel 20 of outer hub 14 is received. Slot 19 is sized so as to be at least slightly larger in width and depth than wheel 20 such that wheel 20 may freely rotate within slot 19. A distal rotational surface 22 of outer hub 14 is located on one side of wheel 20 and a proximal rotational surface 24 located on another side of wheel 20. Rotary surfaces 22, 24 engage handpiece 12 on the sides of slot 19 (see FIG. 1). In one embodiment, wheel 20 may also include spokes 26 separated by grooves 28 such to provide an easy thumb grip for selectively rotating outer hub 14 within slot 19 in either direction (see FIG. 2).

Outer cannula 18 (see FIG. 1) is inserted through an outer hub channel 30 (See FIG. 3) that extends through outer hub 14. Outer cannula 18 is fixed to a channel wall 32, but a distal end 31 of outer cannula 18 is positioned so as to extend a predetermined distance away from handpiece 12. Since outer cannula 18 is fixed to outer hub 14, when outer hub 14 is rotated, outer cannula 18 also rotates and maintains circumferential alignment with outer hub 14.

Outer hub 14 also may include one or more guide holes 34 extending inwardly from a rear surface of outer hub 14. Each guide hole 34 receives one end 35 of a guide pin 36 that is fixedly secured within guide hole 34. Guide pin 36 may be retained in guide hole 34 using conventional methods such as frictional contact, press-fit, welding, or gluing. The opposite end 37 of guide pin 36 is received within a slot 38 formed on inner hub 16, as best seen in FIGS. 1 and 7.

Figure 3:
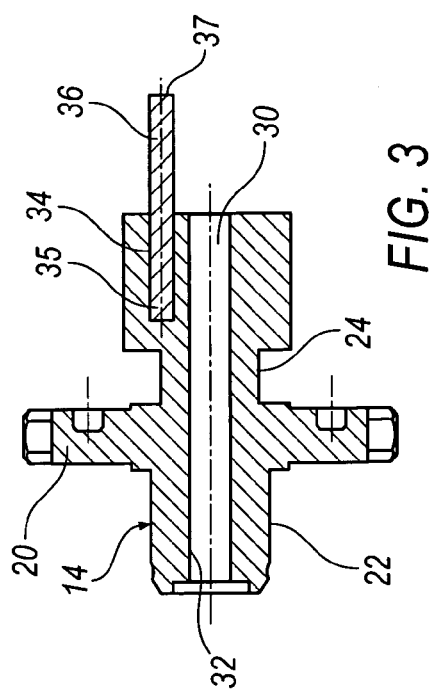
FIG. 3 is a cross-sectional view of an embodiment of an outer hub and a guide for use in the rotating surgical system of FIG. 1.

Although guide pin 36 is embodied as a pin connector in FIG. 3, guide pin 36 may be any connecting member that rotably connects outer hub 14 to inner hub 16. In such a case, guide pin 36 may be round, flat, rectangular, a flange, or a tab. In other cases, guide pin 36 may be molded as an integral part of outer hub 14 or inner hub 16. Alternatively, guide pin 36 may be molded as an element that is part of both outer hub 14 and inner hub 16. The two molded portions would be configured to engage to form guide pin 36. Guide pin 36 may also be loosely received by mounting members in both outer hub 14 and inner hub 16. Additionally, guide pin 36 may be embodied as a portion of a flat sheet that is fixedly attached to both outer hub 14 and inner hub 16.

Figure 4:
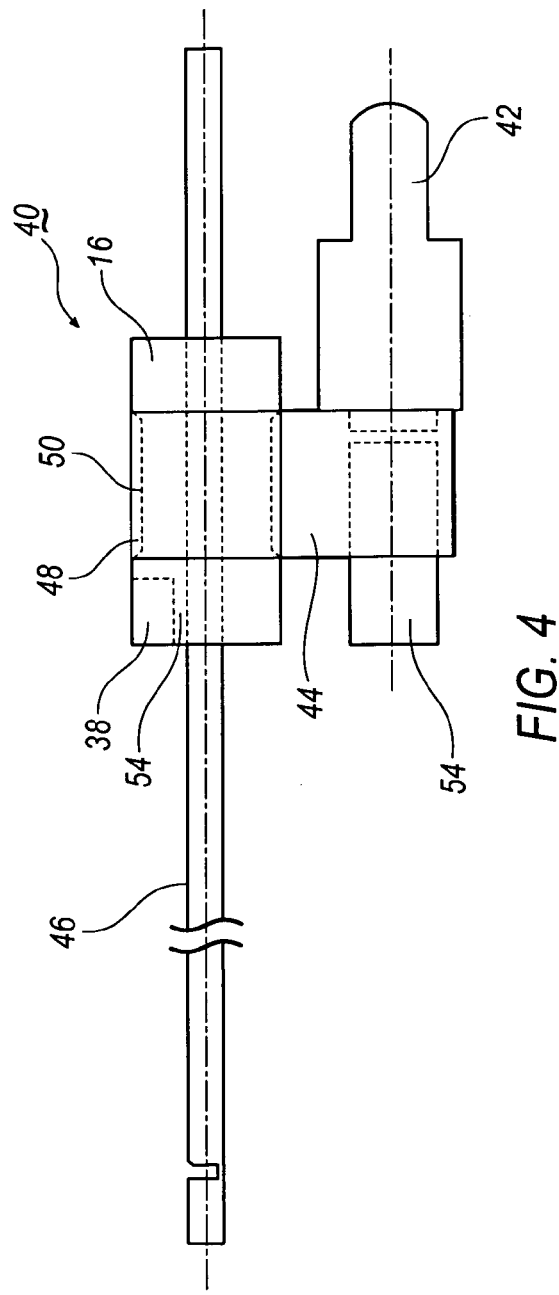
FIG. 4 is a side view of a drive system for use with the rotating surgical system of FIG. 1.

FIG. 4 is a side view of a drive system 40 of which inner hub 16 is a part. In addition to inner hub 16, drive system 40 includes a cam follower 42, a drive member 44, and an inner cannula 46 for use with rotating surgical system 10 of FIG. 1. Inner cannula 46 is affixed to inner hub 16 through a channel that extends through inner hub 16 such that inner cannula 46 axially extends through inner hub 16. Drive member 44 is rotatably attached to inner hub 16 by a ring 48 that circumferentially surrounds inner hub 16. Drive member 44 does not rotate, but rather, provides reciprocative motion to inner hub 16. Ring 48 rides in a groove 50 that allows inner hub 16 to rotate freely with respect to drive member 44.

Reciprocating motion may be introduced into rotating surgical system 10 by a cam (not shown) and cam follower 42. When cam follower 42 engages the cam (not shown), drive member 44 is necessarily driven. Return force for the reciprocative motion is provided by a force closing spring 52 (see FIG. 1) that rides along a spring guide 54. Because inner hub 16 and inner cannula 46 are attached to drive member 44 by ring 48, they are driven by cam follower 42 in a reciprocative manner. Further, because ring 48 rides in groove 50, the reciprocative motion is transmitted to inner hub 16.

Figure 5A:
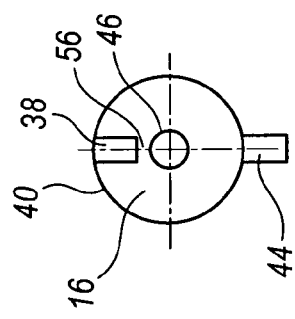
FIG. 5A is a front view of an embodiment of an inner hub for use with the rotating surgical system of FIG. 1.
Figure 5B:
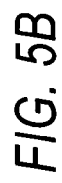
FIG. 5B is a front view of an alternative embodiment of an inner hub for use with the rotating surgical system of FIG. 1.

FIGS. 5A and 5B illustrate alternative embodiments of inner hub 16. In a first embodiment, inner hub 16 includes slot 38. Slot 38 is a channel or notch that extends radially inwardly from an outside surface 40 of inner hub 16. Slot 38 may begin a radial distance away from inner cannula 46 leaving a land area 56 around inner cannula 46 (illustrated in FIGS. 4 and 5A). In a second embodiment, inner hub 16' may be provided with a slot 38' that directly extends from the channel that receives inner cannula 46 to outside surface 40' of inner hub 16, as shown in FIG. 5b.

As stated above, guide pin 36 engages inner hub 16 at slot 38. Accordingly, when outer hub 14 is rotated, slot 38 allows guide pin 36 to rotate inner hub 16 because inner hub 16 is rotatably mounted to drive member 44 by ring 48. Guide pin 36 provides a rotational force to inner hub 16 at a predetermined distance from the axis of inner hub 16. Since inner cannula 46 is affixed to inner hub 16, when outer hub 14, outer cannula 18 and guide pin 36 are rotated, inner hub 16 and inner cannula 46 are also rotated.

The mounting members for guide pin 36, such as slots 38, 38' may also be embodied as holes or specially shaped cavities configured to receive guide pin 38. In an alternative embodiment, the mounting member may be formed in inner cannula 46. The mounting member may be configured as a slot disposed upon inner cannula 46 for receiving a pin that would allow reciprocative motion while also forcing inner cannula 46 to rotate with outer cannula 18. Such a system may include a skirt around the pin that would cover the mounting member slot so as to maintain a vacuum introduced within inner cannula 46.

If reciprocating motion is desired, as is with the exemplary embodiment illustrated in FIG. 7, guide pin 36 may also be slidably received by slot 38 in inner hub 16. When guide pin 36 is received by slot 38, inner hub 16 is configured to allow for axial reciprocation of inner hub 16. As inner hub 16 reciprocates axially, guide pin 36 slides along the length of slot 38. While guide pin 36 is slidably received by slot 38, inner hub 16 maintains the ability to rotate inner cannula 46 with relation to outer hub 14 and guide pin 36.

Referring to FIGS. 3-7, guide pin 36 is attached to outer hub 14 and rotatably connects outer hub 14 to a cutting system 100 (best shown in FIG. 7) that includes components housed in outer cannula 18. Cutting system 100 includes a selectively reciprocating cutter 58 (best shown in FIG. 6A) that includes a tissue receiving opening 60 formed in outer cannula 18 adjacent distal end 31 of outer cannula 18 and selectively reciprocating inner cannula 46.

In operation, inner cannula 46 reciprocates within outer cannula 18 moving a distal end 64 of inner cannula 46 toward and away from distal end 31 of outer cannula 18. A vacuum V is provided by a vacuum port 66 (shown in FIG. 1) that is operably engaged with inner cannula 46. Vacuum V serves to draw tissue 68 through tissue receiving opening 60 formed in outer cannula 18. Distal end 64 of inner cannula 46 is configured to work cooperatively with tissue receiving opening 60 to sever tissue 68 that is pulled through tissue receiving opening 60. More specifically, tissue receiving opening 60 includes a cutting edge 72 configured to work with distal end 64 of inner cannula 46 to sever the tissue.

Inner cannula 46 may also include a hinge 74. Hinge 74 allows distal end 64 of inner cannula 46 to pivot upwardly when a force is applied. In one embodiment, hinge 74 is configured as a slot partially cut radially through inner cannula 46.

As inner cannula 46 engages tissue 68 that is pulled through outer cannula 18, a force F is developed on distal end 64 from the pushing force upon inner cannula 46 and the contact of distal end 64, tissue 68, and cutting edge 72. Force F pivots distal end 64 of inner cannula 46 in a clockwise direction R due to hinge 74 that is cut into inner cannula 46. Pivot R allows for a narrow gap alignment between a top portion 73 of distal end 64 and cutting edge 72, resulting in an essentially zero clearance. This narrow gap provides for first-cut severing of tissue 68 at cutting edge 72. Once severed tissue 76 (see FIG. 6A) is cut free, vacuum V may pull severed tissue 76 along inner cannula 46 to be captured in a collection canister (not shown).

For reciprocating cutter 58 to operate properly, hinge 74 is aligned with cutting edge 72 and tissue receiving opening 60 such that when tissue 68 is pulled within outer cannula 18, distal end 64 of inner cannula 46 will pivot upwardly in order to cut tissue 68 against cutting edge 72. One disclosed embodiment maintains proper alignment of hinge 74 and cutting edge 72 through the cooperation of outer hub 14, guide pin 36, and inner hub 16. These elements maintain alignment of inner cannula 46 and outer cannula 18, even while inner hub 16 and inner cannula 46 reciprocate.

FIG. 6B illustrates outer cannula 18 and inner cannula 46 in a first pivotal position near distal end 64 of inner cannula 46 where inner cannula 46 is pivoted up near cutting edge 72. FIG. 6C illustrates outer cannula 18 and inner cannula 46 in a second pivotal position. As illustrated, the pivoted portion of inner cannula 46 maintains orientation with cutting edge 72 of outer cannula 18. Thus, cutting system 100 maintains circumferential alignment of inner cannula 46 and outer cannula 18 when reciprocating cutter 58 is rotated.

Referring to FIGS. 1 and 7, the operation of rotating surgical system 10 will be described. First, the surgeon determines a comfortable holding position for handpiece 12. Next, the surgeon determines where outer cannula 18 will enter the patient relative to the lesion that is to be removed. Distal end 31 of outer cannula 18 is then inserted into the surgical site such that tissue receiving opening 60 is located near the lesion that is to be removed. The surgeon may then rotate outer hub 14 which is affixed to outer cannula 18 by turning wheel 20. Rotation of outer hub 14 thus rotates tissue receiving opening 60 that is formed on outer cannula 18 adjacent distal end 62 to an appropriate angle to access the lesion. Guide pin 36, which is attached to outer hub 14, is attached to inner hub 16 by engaging slot 38, 38'. Inner cannula 46 is affixed to inner hub 16. Thus, outer hub 14, guide pin 36, and an inner hub 16 work together to rotate outer cannula 18 and inner cannula 46 such that the axial components may remain in the same relative position to one another (i.e. circumferential alignment or angular alignment).

Indeed, for a handpiece 12 that is part of an ergonomic system, the present embodiments permit selective rotation of handpiece 12 within the surgeon's hand to selectively position tissue receiving opening 60. Moreover, rotation of outer cannula 18 also permits simultaneous rotation of other elements of cutting system 100. For example, as inner cannula 46 rotates, alignment of hinge 74 and tissue receiving opening 60 is maintained (see FIG. 6A). A guide space 78 is provided in slot 38 that allows for reciprocation of inner hub 16. Inner hub 16 may thus reciprocate and still maintain contact with guide pin 36. As illustrated, this exemplary embodiment facilitates rotation of inner cannula 46 and outer cannula 18 together such that tissue receiving opening 60 is maintained in proper alignment with hinge 74.

Further, the exemplary embodiment also allows for rotation of cutting system 100 while maintaining the desired ergonomic holding position of handpiece 12 (see FIG. 1). Indeed, surgical system 10 allows the surgeon to hold handpiece 12 while rotating tissue receiving opening 60 independently. As the surgeon rotates outer hub 14, outer cannula 18 and inner cannula 46 are rotated synchronously such that tissue receiving opening 60 and hinge 74 rotate in unison with each other. Thus, the surgeon need not hold handpiece 12 in an awkward or uncomfortable position in order to change the orientation of tissue receiving opening 60.

Additionally, rather than holding handpiece 12, the surgeon may also employ a surgical stabilizing system whereby the surgeon is not required to hold handpiece 12 during the medical procedure. The stabilizing system may be embodied as an immobilized endoscope. In such a system, handpiece 12 may be attached to the stabilizing system using one or more handpiece guides 15. Handpiece guides 15 may be slid into receiving holes on the stabilizing system designed to hold handpiece 12 for surgical operations. Once handpiece 12 is stabilized, the surgeon may position the stabilizing system for the surgical operation much like the hand-guided operation. After handpiece 12 is positioned, tissue receiving opening 60 may be selectively rotated by outer hub 20 for access to the lesion.

The present invention has been particularly shown and described with reference to the foregoing embodiments, which are merely illustrative of the best modes for carrying out the invention. It should be understood by those skilled in the art that various alternatives to the embodiments of the invention described herein may be employed in practicing the invention without departing from the spirit and scope of the invention as defined in the following claims. It is intended that the following claims define the scope of the invention and that the method and apparatus within the scope of these claims and their equivalents be covered thereby. This description of the invention should be understood to include all novel and non-obvious combinations of elements described herein, and claims may be presented in this or a later application to any novel and non-obvious combination of these elements. Moreover, the foregoing embodiments are illustrative, and no single feature or element is essential to all possible combinations that may be claimed in this or a later application.

What is claimed is:

1. A rotating surgical system comprising:
   a base;
   a cavity disposed in said base;
   an outer cannula rotatably engaged with and extending through a portion of said cavity;
   an inner cannula partially positioned within said outer cannula;
   a connecting element operatively connecting said inner cannula to said outer cannula, such that said inner cannula is fixed rotationally with said outer cannula; and
   a cam member operatively coupled to a cam follower to impart reciprocative motion to a drive member connected to said inner cannula,
   wherein said connecting element is secured to an outer cannula hub such that a connecting portion of said connecting element extends proximally therefrom and is configured to be received within a slot extending inwardly from an outer surface of an inner cannula hub.

2. The system of claim 1, wherein said inner cannula oscillates.

3. The system of claim 1, wherein said drive member is engaged with said inner cannula hub, wherein said inner cannula hub has a portion of said inner cannula connected within a channel therein, said drive member providing reciprocative motion to said inner cannula by moving said inner cannula hub.

4. The system of claim 1, further comprising:
   a tissue receiving opening formed in said outer cannula; and
   a cutting portion disposed upon said outer cannula at said tissue receiving opening;
   wherein said inner cannula further includes a hinge formed therein to pivot a distal end of said inner cannula toward said tissue receiving opening, and wherein the rotating surgical system maintains circumferential alignment of said tissue receiving opening and said cutting portion relative to each other.

5. The system of claim 1, said base further including a drive receiver that is configured to receive a drive force.

6. A rotating surgical instrument comprising:
   a first hub adapted to be selectively rotated;
   an outer cannula engaged with said first hub, where said hub provides a rotational force to said outer cannula such that when said first hub is rotated, outer cannula rotates;
   a second hub;
   an inner cannula engaged with said second hub, wherein said inner cannula extends through said first hub and a portion of a drive member; and
   a guide attached to one of said first hub and said second hub and received in a slot that extends inwardly from an outer surface of an end face of the other of said first hub and said second hub, wherein the guide rotatably connects said first hub and said second hub together, said first hub providing a rotational force to the second hub through said guide;
   whereby said outer cannula and said inner cannula are rotationally fixed together;
   wherein the drive member is configured to move said second cannula hub in a first direction;
   a biasing member operatively connected to the drive member and configured to bias the second cannula hub, thereby positioning the inner cannula in a retracted configuration; and
   a base, wherein said base includes a cavity disposed within said base, wherein said cavity is configured to receive said first and second hubs therein.

7. The instrument of claim 6, wherein part of said inner cannula reciprocates within said outer cannula.

8. The instrument of claim 7, wherein said guide attaches to said first hub and slidably engages with said slot in said second hub.

9. The instrument of claim 7, wherein:
   said second hub is configured to reciprocate while maintaining a rotary connection with said guide.

10. The system of claim 1, further comprising a spring configured to impart a return force so as to position said inner cannula in a retracted configuration.

11. The system of claim 1, further comprising an outer cannula hub that includes a wheel member configured for selective rotation.

* * * * *